US008394582B2

(12) United States Patent
Bohmer

(10) Patent No.: US 8,394,582 B2
(45) Date of Patent: Mar. 12, 2013

(54) IDENTIFICATION OF FETAL DNA AND FETAL CELL MARKERS IN MATERNAL PLASMA OR SERUM

(75) Inventor: Ralph Michael Bohmer, St. Kilda (AU)

(73) Assignee: Genetic Technologies, Inc (AU)

( * ) Notice: Subject to any disclaimer, the term of this patent is extended or adjusted under 35 U.S.C. 154(b) by 476 days.

(21) Appl. No.: 10/547,721

(22) PCT Filed: Mar. 5, 2004

(86) PCT No.: PCT/AU2004/000287
§ 371 (c)(1),
(2), (4) Date: Jun. 13, 2006

(87) PCT Pub. No.: WO2004/078999
PCT Pub. Date: Sep. 16, 2004

(65) Prior Publication Data
US 2007/0134658 A1    Jun. 14, 2007

Related U.S. Application Data

(60) Provisional application No. 60/451,658, filed on Mar. 5, 2003, provisional application No. 60/451,657, filed on Mar. 5, 2003, provisional application No. 60/457,656, filed on Mar. 5, 2003, provisional application No. 60/457,855, filed on Mar. 27, 2003.

(51) Int. Cl.
G01N 33/53     (2006.01)
C12N 5/00      (2006.01)
C12N 5/02      (2006.01)

(52) U.S. Cl. .............................. 435/6; 435/7.1; 435/325

(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,153,117 A | 10/1992 | Simons | |
| 5,447,842 A | 9/1995 | Simons | |
| 5,503,981 A | 4/1996 | Mueller et al. | |
| 5,541,072 A | 7/1996 | Wang et al. | |
| 5,641,870 A | 6/1997 | Rinderknecht et al. | |
| 5,750,339 A * | 5/1998 | Smith ............................ | 435/6 |
| 5,798,276 A | 8/1998 | Haugland et al. | |
| 5,830,912 A | 11/1998 | Gee et al. | |
| 5,969,157 A | 10/1999 | Vicenzi | |
| 6,130,101 A | 10/2000 | Mao et al. | |
| 6,162,931 A | 12/2000 | Gee et al. | |
| 6,927,028 B2 * | 8/2005 | Dennis et al. ........................ | 435/6 |
| 2003/0211522 A1 * | 11/2003 | Landes et al. ........................ | 435/6 |
| 2005/0287604 A1 | 12/2005 | Bohmer | |

FOREIGN PATENT DOCUMENTS

| | | |
|---|---|---|
| WO | WO 91/14768 | 10/1991 |
| WO | WO 97/14028 | 4/1997 |
| WO | WO 02/26891 | 4/2002 |

OTHER PUBLICATIONS

Bohmer Intervirology 1998, v.41, pp. 226-231.*
Warwick Lancet, 1994, v.2, p. 344.*
"Non-Invasive Determination of the Paternal HLA Haplotype of a Fetus Using Kinetic PCR to Detect Fetal Microchimerism in Maternal Plasma" by Reed et al., Bone Marrow Transplantation (2002) 29, 527-529.
"Prenatal Diagnosis Using Fetal Cells and Free Fetal DNA in Maternal Blood" by Holzgreve et al., Clinics in Perinatology, vol. 28, No. 2, Jun. 2001, pp. 353-365.
"Cell-Free Fetal DNA and Intact Fetal Cells in Maternal Blood Circulation: Implications for First and Second Trimester Non-Invasive Prenatal Diagnosis" by Bischoff et al., European Society of Human Reproduction and Embryology, Human Reproduction Update, vol. 8, No. 6, pp. 493-500, 2002.
"Fetal DNA in Maternal Plasma: Biology and Diagnostic Applications" by Lo, Clinical Chemistry 46:12, pp. 1903-1906 (2000).
"Microchimerism and HLA-Compatible Relationships of Pregnancy in Scleroderma", by Nelson et al., The Lancet, vol. 351, Feb. 21, 1998, pp. 559-562.
"Differential DNA Methylation Between Fetus and Mother As a Strategy for Detecting Fetal DNA in Maternal Plasma" by Poon, Clinical Chemistry 48:1, pp. 35-41, (2002).
Al-Mufti et al., "Investigation of Maternal Blood Enriched for Fetal Cells: Role in Screening and Diagnosis of Fetal Trisomies"; 1999; American Journal of Medical Genetics; 85; pp. 66-75.
Bianchi, "Fetal Cells in the Mother: From Genetic Diagnosis to Diseases Associated With Fetal Cell Microchimerism"; 2000; European Journal of Obstetrics & Gynecology and Reproductive Biology; 92; pp. 103-108.
Bussel et al., "Antenatal Treatment of Neonatal Alloimmune Thrombocytopenia", The New England Journal of Medicine 319:1374-1378, Nov. 24, 1988.
Coppola et al., "High-Performance Liquid Chromatography of Amino Acids, Peptides and Proteins: XCI liB. Comparison of Methods for the Purification of Mouse Monoclonal Immunoglobulin M Autoantibodies"; 1989; Journal of Chromatography; 476; pp. 269-290.

(Continued)

Primary Examiner — Michail Belyavskyi
(74) Attorney, Agent, or Firm — Sheridan Ross P.C.

(57) ABSTRACT

The present invention relates to the identification of fetal specific nucleic acids and fetal cell markers in maternal plasma or serum. In particular, the present invention relates to methods which rely on the analysis of polymorphic alleles of a population to determine an allele which is possessed by the fetus but absent from the mother. Fetal specific alleles identified using the methods of the invention can be used to quantify fetal DNA from maternal plasma or serum. In addition, antigens encoded by alleles identified using the methods of the invention can be targeted in methods of isolating or detecting fetal cells.

15 Claims, 2 Drawing Sheets

OTHER PUBLICATIONS

Figure 1:
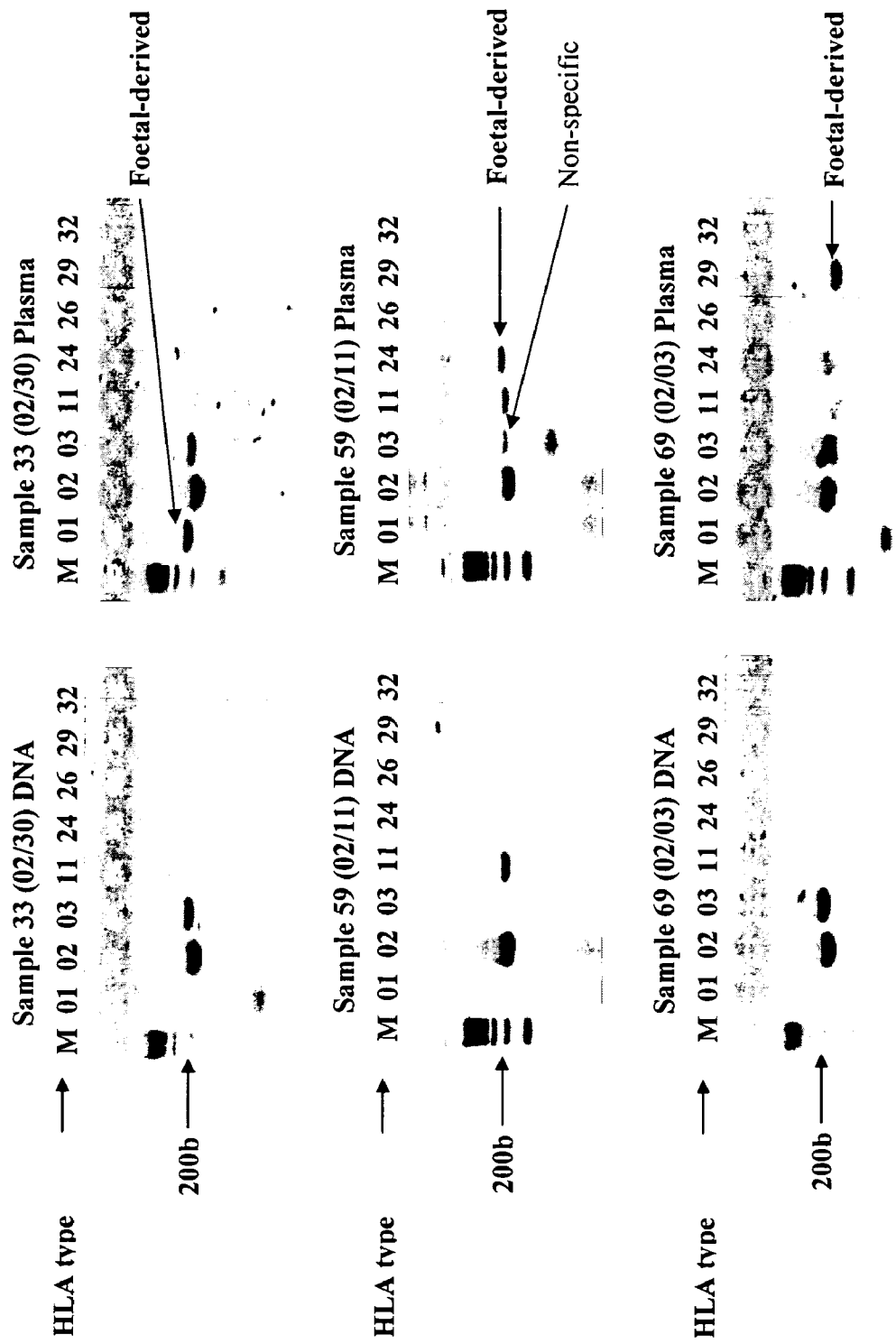

Douglas et al., "Trophoblast in the Circulating Blood During Pregnancy"; Nov. 1959; American Journal of Obstetrics & Gynecology; V. 78; No. 5; pp. 960-973.

Folkersen et al., "An Immunoprecipitation-Dissociation Technique for Large Scale Antibody Purification and an Antigen Consumption Electroimmunoassay for Antibody Quantitation. A Model Study with Antibodies to Pregnancy Zone Protein"; 1978; Journal of Immunological Methods; 23; pp. 127-135.

Hoffmann et al., "Continuous Free-Flow Electrophoresis Separation of Cytosolic Proteins from the Human Colon Carcinoma Cell Line LIM 1215: A Non Two-Dimensional Gel Electrophoresis-Based Proteome Analysis Strategy"; 2001; Proteomics; 1; pp. 807-818.

Mowbray et al., "Maternal response to Paternal Trophoblast Antigens", American Journal of Reproductive Immunology, 1997, vol. 37, pp. 421-426.

Nevens et al., "Affinity Chromatographic Purification of Immunoglobulin M Antibodies Utilizing Immobilized Mannan Binding Protein"; 1992; Journal of Chromatography; 597; pp. 247-256.

Parker et al., "Biophysical Characteristics of Anti-Gala1-3GallgM Binding to Cell Surfaces: Implications for Xenotransplantation"; Feb. 15, 2001; Transplantation; V. 71; pp. 440-446, No. 3.

Reed et al., "The alloantibody response of pregnant women and its suppression by soluble HLA antigens and and anti-idiotypic antibodies", J. Reprod. Immunol., 1992, vol. 20, pp. 115-128.

Schroder, "Transplacental Passage of Blood Cells," Journal of Medical Genetics, 1975, vol. 12, pp. 230-242.

Sisson et al., "An Improved Method for immobilizing IgG antibodies on protein A-agarose," Journal of Immunological Methods, 1990, vol. 127, pp. 215-220.

Szekeres-Bartho et al., "Immunological relationship between the mother and the fetus", Intern. Rev. Immunol., Nov.-Dec. 2002, vol. 21, pp. 471-495.

Tsang et al., "Optimum dissociating condition for immunoaffinity and preferential isolation of antibodies with high specific activity," Journal of Immunological Methods, vol. 138, 1991, pp. 291-299.

Wegmann et al., "Allogeneic Placenta is a Paternal Strain Antigen Immunoabsorbent", The Journal of Immunology 122 (1): 270-274, 1979.

* cited by examiner

```
                      SEQUENCE LISTING

<160> NUMBER OF SEQ ID NOS: 17

<210> SEQ ID NO 1
<211> LENGTH: 21
<212> TYPE: DNA
<213> ORGANISM: Artificial
<220> FEATURE:
<223> OTHER INFORMATION: Oligonucleotide primer

<400> SEQUENCE: 1
tgtatggctg cgacgtgggg c                                           21

<210> SEQ ID NO 2
<211> LENGTH: 19
<212> TYPE: DNA
<213> ORGANISM: Artificial
<220> FEATURE:
<223> OTHER INFORMATION: Oligonucleotide primer
```

```
<400> SEQUENCE: 2
caggtatctg cggagcccg                                                19

<210> SEQ ID NO 3
<211> LENGTH: 19
<212> TYPE: DNA
<213> ORGANISM: Artificial
<220> FEATURE:
<223> OTHER INFORMATION: Oligonucleotide primer

<400> SEQUENCE: 3
ggagccccgc ttcatcgca                                                19

<210> SEQ ID NO 4
<211> LENGTH: 19
<212> TYPE: DNA
<213> ORGANISM: Artificial
<220> FEATURE:
<223> OTHER INFORMATION: Oligonucleotide Primer

<400> SEQUENCE: 4
cgcagggtcc ccaggtcca                                                19

<210> SEQ ID NO 5
<211> LENGTH: 18
<212> TYPE: DNA
<213> ORGANISM: Artificial
<220> FEATURE:
<223> OTHER INFORMATION: Oligonucleotide primer

<400> SEQUENCE: 5
atggctgcga cgtggggt                                                 18

<210> SEQ ID NO 6
<211> LENGTH: 19
<212> TYPE: DNA
<213> ORGANISM: Artificial
<220> FEATURE:
<223> OTHER INFORMATION: Oligonucleotide primer

<400> SEQUENCE: 6
ccactccacg cacgtgcca                                                19

<210> SEQ ID NO 7
<211> LENGTH: 19
<212> TYPE: DNA
<213> ORGANISM: Artificial
<220> FEATURE:
<223> OTHER INFORMATION: Oligonucleotide primer

<400> SEQUENCE: 7
tatggctgcg acgtggggc                                                19

<210> SEQ ID NO 8
<211> LENGTH: 18
<212> TYPE: DNA
<213> ORGANISM: Artificial
<220> FEATURE:
<223> OTHER INFORMATION: Oligonucleotide primer

<400> SEQUENCE: 8
cctccaggta ggctctct                                                 18

<210> SEQ ID NO 9
<211> LENGTH: 19
```

```
<212> TYPE: DNA
<213> ORGANISM: Artificial
<220> FEATURE:
<223> OTHER INFORMATION: Oligonucleotide primer

<400> SEQUENCE: 9
acaccctcca gatgatgtt                                                    19

<210> SEQ ID NO 10
<211> LENGTH: 19
<212> TYPE: DNA
<213> ORGANISM: Artificial
<220> FEATURE:
<223> OTHER INFORMATION: Oligonucleotide primer

<400> SEQUENCE: 10
ccctccaggt aggctctct                                                    19

<210> SEQ ID NO 11
<211> LENGTH: 21
<212> TYPE: DNA
<213> ORGANISM: Artificial
<220> FEATURE:
<223> OTHER INFORMATION: Oligonucleotide primer

<400> SEQUENCE: 11
tccatgaggt atttctacac c                                                 21

<210> SEQ ID NO 12
<211> LENGTH: 18
<212> TYPE: DNA
<213> ORGANISM: Artificial
<220> FEATURE:
<223> OTHER INFORMATION: Oligonucleotide primer

<400> SEQUENCE: 12
gcagggtccc caggttcg                                                     18

<210> SEQ ID NO 13
<211> LENGTH: 21
<212> TYPE: DNA
<213> ORGANISM: Artificial
<220> FEATURE:
<223> OTHER INFORMATION: Oligonucleotide primer

<400> SEQUENCE: 13
cccactccat gaggtatttc a                                                 21

<210> SEQ ID NO 14
<211> LENGTH: 19
<212> TYPE: DNA
<213> ORGANISM: Artificial
<220> FEATURE:
<223> OTHER INFORMATION: Oligonucleotide primer

<400> SEQUENCE: 14
ctcctgctct atccacggt                                                    19

<210> SEQ ID NO 15
<211> LENGTH: 21
<212> TYPE: DNA
<213> ORGANISM: Artificial
<220> FEATURE:
<223> OTHER INFORMATION: Oligonucleotide primer

<400> SEQUENCE: 15
ccactccatg aggtatttct t                                                 21
```

```
<210> SEQ ID NO 16
<211> LENGTH: 18
<212> TYPE: DNA
<213> ORGANISM: Artificial
<220> FEATURE:
<223> OTHER INFORMATION: Oligonucleotide primer

<400> SEQUENCE: 16
gtagcggacc gcgatccg                                                        18

<210> SEQ ID NO 17
<211> LENGTH: 36
<212> TYPE: DNA
<213> ORGANISM: Artificial
<220> FEATURE:
<223> OTHER INFORMATION: Oligonucleotide

<400> SEQUENCE: 17
gctcgggtga cgacacgcag ttcgtgcgga ccgagc                                    36
```

IDENTIFICATION OF FETAL DNA AND FETAL CELL MARKERS IN MATERNAL PLASMA OR SERUM

CROSS-REFERENCE TO RELATED APPLICATIONS

This application claims the priority benefit of U.S. Provisional Application No. 60/451,658, filed Mar. 5, 2003; U.S. Provisional Application No. 60/451,657, filed Mar. 5, 2003, U.S. Provisional Application No. 60/451,656, filed Mar. 5, 2003, and U.S. Provisional Application No. 60/457,855, filed Mar. 27, 2003, all of which are incorporated herein by reference in their entirety. This application is a national phase filing of PCT/AU2004/000287, filed Mar. 5, 2004, also incorporated herein by reference in its entirety.

FIELD OF THE INVENTION

The present invention relates to the identification of fetal specific nucleic acids and fetal cell markers. In particular, the present invention relates to the identification of alleles of fetal DNA which are not present in the genome of the mother. Fetal specific alleles identified using the methods of the invention can be used to quantify fetal DNA in a sample comprising fetal and maternal nucleic acids. In addition, antigens encoded by alleles identified using the methods of the invention can be targeted in methods of isolating or detecting fetal cells.

BACKGROUND OF THE INVENTION

Currently, fetal diagnosis is generally carried out by a procedure known as amniocentesis which involves the aspiration of a small sample of amniotic fluid from the pregnant mother, culturing the fetal cells in the fluid, and determining the karyotype of the fetal cells. Recently, chorionic villus sampling has also been used, which involves the direct transcervical and transabdominal aspiration of the chorionic villus. However, as both amniocentesis and chorionic villus sampling require invasive procedures for obtaining fetal cells, they inevitably expose both the mother and the fetus to a certain amount of risk. Accordingly non-invasive approaches to prenatal diagnosis are preferred.

Cell-free fetal DNA circulates in the plasma of pregnant women (Lo et al., 1997). Up to at least 7% of all cell-free DNA in maternal plasma/serum has been found to be of fetal origin. It has been demonstrated that this fetal DNA can be used to predict the gender of the fetus (Lo et al., 1997), as well as to determine the fetal Rhesus D status (Lo et al., 1998).

Studies have also indicated that the amount of fetal DNA in maternal plasma/serum can be correlated with certain fetal abnormalities such as trisomy 21 (Down syndrome) (Lee et al., 2002) and trisomy 13 (Wataganara et al., 2003). Thus far, the quantitation of fetal DNA has generally relied upon Y-chromosome-specific sequences, which cannot serve to measure the DNA of female fetuses. Accordingly, a gender-independent quantitation of fetal DNA is needed.

There is a need for further methods which identify fetal specific nucleic acids and fetal cell specific markers. In particular, markers that are gender independent are required which can be detected through non-invasive procedures.

SUMMARY OF THE INVENTION

The present inventor has devised methods for identifying gender independent markers of fetal specific nucleic acids and fetal cells in a pregnant female. These methods rely on the analysis of polymorphic alleles of a population to determine an allele which is possessed by the fetus but absent from the mother. These methods can be performed in a non-invasive manner through the analysis of samples comprising fetal and maternal nucleic acids obtained from the pregnant female.

In a first aspect, the present invention provides a method of identifying an allele of a fetal cell, said allele not being present in maternal cells, the method comprising;
 i) identifying alleles which are not present in maternal cells,
 ii) obtaining a sample from the mother comprising fetal and maternal nucleic acids, and
 iii) screening nucleic acids from the sample for at least one allele not present in the maternal cells.

Steps i) and ii) can be performed in any order.

The general principle of the method of the first aspect can be applied by typing all alleles at a particular locus, whether derived from the fetus or the mother. Thus, in a second aspect the present invention provides a method of identifying an allele of a fetal cell, said allele not being present in maternal cells, the method comprising;
 i) obtaining a sample from the mother comprising fetal and maternal nucleic acids,
 ii) typing at least one locus from the sample obtained in step i),
 iii) comparing the alleles identified in step ii) with alleles of the same locus possessed by the mother, and
 iv) selecting an allele typed in step iii) which is not possessed by the mother.

Any allele typed in step ii) of the second aspect which is not possessed by the mother will be a fetal marker inherited from the father. The method of the second aspect differs from that of the first aspect, as the first relies on initially identifying alleles that, if possessed by the fetus, would be fetal specific followed by screening the sample for such potential fetal specific alleles, whereas the second aspect examines all alleles in nucleic acids obtained from the sample at a given locus (both fetal and maternally derived) followed by excluding those which are found in the mother to identify a fetal marker.

Step ii) of the second aspect may identify from the sample up to three alleles at a given locus, two from the maternal nucleic acids and one from the fetal nucleic acids which has been inherited from the father. Naturally, the fetal nucleic acids will comprise a second allele which has been inherited by the mother, however, it will typically not be distinguished (unless a mutation has occurred) from that of the mother. More specifically, a primer amplifying a specific maternal allele, which was also inherited by the fetus, will amplify a single product from two sources, namely the maternal genome and the fetal genome. At the other end of the scale the father and mother may be homozygous for the same allele, and step ii) will only identify a single allele. If such a case arises, or if the fetus has inherited an allele from the father which is also possessed by the mother, other loci will need to be examined to identify a fetal marker. Preferably, many loci are typed in a single reaction so that if one locus cannot be used as a marker the method will identify a marker at another locus.

An important advantage of the above methods is that they do not require that the genotype of the father at the allele be known or determined. Accordingly, in a particularly preferred embodiment, the father is not typed for any alleles.

In instances where the father is known, the methods may further comprise typing the father at the same locus/loci as the mother, and identifying alleles which are not present in the mother but which are present in the father. Although the combination of the maternal and paternal typing will provide a list of alleles which may be present in fetal DNA, if the father is heterozygous at a given locus the maternal sample comprising fetal and maternal nucleic acids will still need to be screened for fetal specific alleles to unequivocally identify at least some fetal markers as it cannot be predicted which one of the heterozygous alleles would have been inherited by the fetus.

The methods can be performed at any stage during pregnancy. However, in a preferred embodiment, the sample is obtained during the first trimester of pregnancy.

The present invention relies on the genotype of the mother at the allele being investigated being known. Such alleles may have previously been characterized for other reasons, such as if it is the mothers second child and the method of the first or second aspect was performed during her first pregnancy, or the mother has had an organ transplantation and hence the mother was HLA typed. However, in many cases the genotype of the mother of the allele(s) being investigated will be unknown. In such circumstances, the methods will further comprise typing alleles of at least one locus of the mother. Naturally, the typing of the mother will at least target the same locus being investigated in the methods of the first and second aspects. With regard to the first aspect, the maternal typing will be performed before step i).

The mother can be typed using any technique known in the art. This procedure can be performed at a single locus or a number of loci. For instance, the typing can be performed by obtaining a genomic DNA sample from the mother and exposing the DNA to amplification and/or sequencing procedure. In another example, the typing is performed by using antibodies which bind the protein products of specific alleles. Preferably, the locus (loci) that are analysed encode proteins (antigens) that can be found on the cell surface and can bind antibodies directed against the protein.

The sample from which the maternal typing is performed can be any tissue including, but not limited to, nucleated blood cells, saliva and hair follicles. It is preferred that the sample is obtained with as little discomfort to the mother as possible. In a particularly preferred embodiment, the sample comprises nucleated blood cells, such as T and B lymphocytes, macrophages etc, obtained from a blood sample taken from the mother.

The maternal typing should preferably be performed on a sample free from fetal nucleic acids. Considering the quantity of fetal DNA typically found in maternal plasma or serum samples it is preferred that such maternal plasma or serum samples are not used for typing the mother. Although the cellular fraction of a maternal blood sample has been reported to contain fetal cells, it is known in the art that these fetal cells are not in a sufficiently high enough concentration to interfere with standard typing techniques. Thus, if the sample for maternal typing is contaminated with fetal nucleic acids the level of contamination will be sufficiently low such that it does not interfere with the accurate typing of the mother.

In a particularly preferred embodiment, a blood sample is taken from the mother and the plasma and cellular fractions separated by centrifugation, with the cellular fraction being utilized to type the mother and the plasma fraction being used as the source of fetal nucleic acids.

Although it is preferable that typing the mother directly characterizes an allele, or protein (antigen) encoded thereby, the method may comprise typing by analysing markers, such as single nucleotide polymorphisms or repeat number polymorphisms, that are linked to a particular allele. Such linked polymorphic markers may be coding or non-coding.

Similarly, although it is preferred that the fetal nucleic acids from the sample comprising fetal and maternal nucleic acids are directly analysed for a specific allele(s), the method may comprise typing by analysing markers, such as single nucleotide polymorphisms or repeat number polymorphisms, that are linked to a particular allele.

The allele may be any polymorphism existing within the population. Preferably, the polymorphism is within a gene. More preferably, the polymorphism is within an exon of a gene which encodes a protein. Even more preferably, the polymorphism is within an exon of a gene which encodes a protein such that the amino acid sequence of the encoded protein varies between some members of the population.

In a particularly preferred embodiment, the allele is from an HLA locus. Thus, a preferred embodiment of the first aspect comprises a method of identifying an HLA allele of a fetal cell, said allele not being present in maternal cells, the method comprising;
  i) identifying HLA alleles which are not present in maternal cells,
  ii) obtaining a sample from the mother comprising fetal and maternal nucleic acids, and
  iii) screening nucleic acids from the sample for at least one HLA allele not present in the maternal cells.

Furthermore, a preferred embodiment of the second aspect comprises a method of identifying an HLA allele of a fetal cell, said allele not being present in maternal cells, the method comprising;
  i) obtaining a sample from the mother comprising fetal and maternal nucleic acids,
  ii) HLA typing at least one HLA locus from the sample obtained in step i),
  iii) comparing the HLA alleles identified in step ii) with HLA alleles of the same locus possessed by the mother, and
  iv) selecting an HLA allele typed in step iii) which is not possessed by the mother.

Any or all of the HLA genes may be analysed, including those of class I, class II or class III, using the method of the first or second aspect. Preferably, at least some of the class I or class II HLA alleles are typed.

Screening the nucleic acids from the sample for at least one HLA allele specific for a fetal cell can be performed using any technique known in the art. In a preferred embodiment, the nucleic acid is subjected to amplification-based HLA typing procedures. In a particularly preferred embodiment, the nucleic acid is subjected to sequence specific primer (SSP) typing using a multitude of allele specific primer pairs.

As is known in the art, the HLA complex is highly polymorphic. Many polymorphisms within, for example humans, have been characterized, and the frequency within which a given allele exists in at least some specific populations (e.g. geographic and/or race) has been determined. Upon characterizing a HLA allele of the mother at a given locus, known polymorphisms can readily be screened to determine relevant HLA alleles which occur in the population but are not possessed by the mother.

Preferably, screening nucleic acids from the sample for at least one HLA allele targets HLA alleles which are common in the population but absent in the mother. Naturally, this reduces the number of alleles which need to be analysed before a fetal DNA/cell marker is identified. Preferably, the targeted HLA allele is found within at least 5%, more preferably at least 10% of the population.

The sample comprising fetal and maternal nucleic acids can be obtained from any source known in the art. Examples include, but are not limited to plasma, serum or urine. Preferably, the sample is derived from plasma or serum. Preferably, the serum or plasma sample is subjected to affinity chromatography to enrich nucleic acids from the sample before the method of the first or second aspect is performed.

The nucleic acid can be DNA or RNA. In the instance where the nucleic acid is RNA it is preferred that the RNA is reverse transcribed to produce cDNA. However, it is particularly preferred that the nucleic acid is DNA.

Preferably the mother is a mammal. More preferably the mother is a human.

In another embodiment, the mother can be any organism which comprises a HLA-like complex. An example of a non-human HLA-like complex is the major histocompatibility complex on chromosome 17 in the murine genome.

The fetal specific alleles identified using the methods of the invention can be used to quantify the amount of fetal nucleic acid in a sample that comprises both fetal and maternal nucleic acids. As reported in the literature, such quantification procedures are useful for the diagnosis of various diseases such as fetal trisomy 21.

Thus, in a third aspect the present invention provides a method of quantifying fetal specific nucleic acids in a sample comprising fetal and maternal nucleic acids, the method comprising identifying an allele which is present in the DNA of a fetal cell but absent from maternal DNA using a method according to the invention, and determining the concentration of the allele in the sample.

The quantification of the fetal specific nucleic acid in the sample can be performed using any technique known in the art. Preferably, the allele is quantified by exposing the sample to a nucleic amplification procedure which specifically amplifies the allele, and detecting the amplification product.

Preferably, the allele is an HLA allele.

Furthermore, in a fourth aspect the present invention provides a method of screening for a disease associated with abnormal levels of fetal DNA in the mother, the method comprising identifying an allele which is present in the DNA of a fetal cell but absent from maternal DNA using a method of the invention, and determining the concentration of the allele in a sample obtained from the mother which comprises fetal and maternal nucleic acids.

The abnormal levels of fetal DNA may be higher or lower than those typically found in healthy mothers carrying a fetus which is developing normally. Examples of diseases which have been implicated in being associated with elevated levels of fetal DNA in the mother include, but are not limited to, fetal trisomy 21, fetal trisomy 13, preterm labour, preeclampsia, and idiopathic polyhydramnios.

Preferably, the allele is an HLA allele.

The isolation and/or detection of fetal cells from, for example maternal blood, requires a marker that is specific for the fetal cell. In instances where the allele identified by the first or second aspect encodes a protein, this protein can be considered as a fetal specific marker.

Accordingly, in a fifth aspect the present invention provides a method of isolating fetal cells from a sample, the method comprising identifying an allele, encoding an antigen, which is present in the DNA of a fetal cell but absent from maternal DNA using a method according to the invention, binding to the fetal cell an affinity reagent which recognises the antigen, and selecting cells bound by the affinity reagent.

In a sixth aspect, the present invention provides a method of detecting fetal antigens in a sample, the method comprising identifying an allele, encoding an antigen, which is present in the DNA of a fetal cell but absent from maternal DNA using a method according to the invention, exposing the sample to an affinity reagent which recognises the antigen, and detecting antigen-affinity reagent complexes.

In a seventh aspect, the present invention provides a method of analysing feto-maternal cell-trafficking and/or microchimerism, the method comprising identifying an allele, encoding an antigen, which is present in the DNA of a fetal cell but absent from maternal DNA using a method according to the invention, detecting a fetal cell in a sample obtained from a mother by exposing the sample to an affinity reagent which recognises the antigen, and detecting antigen-affinity reagent complexes.

With regard to the seventh aspect, it is preferred that the disease is scleroderma. Furthermore, it is preferred that the mother has given birth to the child.

With regard to any one of the fifth, sixth or seventh aspects, preferably the sample is the cellular fraction of a blood sample obtained from the mother.

Preferably, the antigen is a cell surface protein. More preferably, the cell surface protein is a HLA protein.

Preferably, the affinity reagent which recognises the antigen is an antibody. More preferably, the antibody is detectably labelled. Alternatively, antibody binding can be detected using a detectably labelled secondary antibody. As is known in the art, the secondary antibody binds the antibody directed against the antigen.

Examples of suitable detectable labels include, but are not limited to, those selected from the group consisting of a radioisotope, a fluorescent compound, a colloidal metal, a chemiluminescent compound, a bioluminescent compound, and an enzyme.

Also provided as an eighth aspect is a method of detecting fetal specific nucleic acids in a sample, the method comprising identifying an allele which is present in the DNA of the fetal cell but absent from maternal DNA using a method of the present invention, exposing the sample to an affinity reagent which recognises the allele, and detecting allele-affinity reagent complexes.

Preferably, the affinity reagent which recognises the allele is a labelled nucleic probe which selectively hybridizes to the allele.

The present inventor has also devised methods of quantifying fetal specific nucleic acids in, for example, a maternal plasma or serum sample using subtractive hybridization based procedures. Accordingly, in a ninth aspect the present invention provides a method of quantifying fetal specific nucleic acids in a sample comprising fetal and maternal nucleic acids, the method comprising using subtractive hybridization to capture nucleic acids from the sample which are either maternal specific or which are shared between the mother and the fetus, and quantifying the remaining nucleic acids.

In one instance, the method relies on differential epigenetic modifications between maternal and fetal DNA. Thus, in particularly preferred embodiment the method of the ninth aspect comprises the following i) obtaining a first sample comprising maternal, but no or small quantities of fetal, DNA, ii) obtaining a second sample comprising fetal and maternal DNA, iii) exposing the first and second sample to an agent that converts one of, but not both, a) a nucleotide or b) the same nucleotide comprising an epigenetic modification, in a manner such that upon synthesis of a complementary sequence the complementary sequence is altered when compared to synthesis in the absence of exposure to the agent, iv) denaturing the DNA from the first sample from iii) and exposing the DNA to conditions which result in the synthesis of a complementary sequence, wherein the complementary sequence is DNA or RNA, v) removing the DNA from iv) that was used as the template during synthesis, vi) denaturing the DNA from the second sample from iii), vii) combining the products of v) and vi) in the same vessel and exposing the products to conditions which promote nucleic acid hybridization, viii) isolating and quantifying the DNA obtained from vii) which is derived from the second sample which has not hybridized to the synthesized DNA or RNA produced in iv).

In this embodiment differences in epigenetic modifications are targeted to synthesize from maternally derived DNA a complementary sequence which is sufficiently different to a complementary sequence synthesized from the corresponding locus of fetal DNA such that the two complementary sequences have differing ability to hybridize to a target molecule synthesized using maternal DNA as a template. More specifically, where a suitable concentration of epigenetic differences exist between maternal and fetal DNA at a particular loci the method will result in the nucleic acid derived from the maternal loci being captured in vii), whilst that derived from the fetal DNA will be isolated in step viii). Whilst at many loci there will not be sufficient differences between epigenetic modifications for the fetal derived molecules to be isolated in step viii), there will be enough regions with such variations to enable step viii) to result in the isolation of a population of nucleic acids which can be used as an indicator of total fetal DNA levels in the sample.

As the skilled addressee would be aware, numerous steps of this embodiment can be rearranged without altering the working of the invention. For example, ii) could be performed after v).

Preferably, the epigenetic modification is methylation of a cytosine.

Preferably, the agent is sodium bisulfite.

Preferably, v) further comprises attaching the synthesized DNA or RNA strand to a solid support. Any suitable solid support may be used such as, but not limited to, beads, plastics, silicon, a polymer matrix, or a membrane.

In a further preferred embodiment, the vessel has two open ends and comprises therein the synthesized DNA or RNA derived from the first sample attached to a solid support. In this embodiment, vii) comprises passing the treated and denatured DNA from the second sample through the column and collecting the eluate.

In yet another preferred embodiment, the synthesis results in the incorporation of a label molecule. The label can be used, for example, to attach the synthesized DNA or RNA to a solid support. In a particularly preferred embodiment, at least some of the nucleotide precursors used in the synthesis procedure are biotinylated, and the synthesized products are attached to a solid support via the biotin label.

In a further preferred embodiment, upon denaturation of the DNA in the first sample, the synthesis is primed by short random oligonucleotide primers (for example random hexamers) in the presence of a suitable polymerase such as, but not limited to, DNA polymerase I from *E. coli*.

In the instance where RNA is produced in the synthesis step, v) may comprise exposing the reaction to DNase to remove the template DNA.

The hybridization and denaturing steps can be performed using techniques known in the art. Preferably, the hybridization is performed under high stringency conditions which promote only closely related sequences to hybridize.

Preferably, the amount of maternal DNA in the first sample is greater than the total DNA in the second sample (which will comprise both fetal and maternal DNA). More preferably, the amount of maternal DNA in the first sample is at least 20-fold higher, more preferably at least 50-fold higher, and even more preferably at least 100-fold higher than the total DNA in the second sample.

The first sample can be obtained from any tissue of the mother which comprises no or small quantities of fetal DNA. As outlined above, some fetal cells may be present in a sample of nucleated blood cells obtained from the mother. However, it is envisaged that such fetal cells will be present at insufficient concentration, namely as low as one fetal cell to a million maternal cells, to prevent the enrichment of fetal specific DNA. Preferably, the first sample is obtained from a tissue known not to comprise fetal DNA or fetal cells such as saliva.

Preferably, the term comprises "small quantities of fetal DNA" means that maternal DNA is found at least at a 100 fold, more preferably at least at a 1,000, and even more preferably at least at a 10,000 fold higher concentration than any contaminating fetal DNA.

In a particularly preferred embodiment, the maternal DNA from the first sample is cleaved into fragments.

Preferably, maternal DNA in the first sample is cleaved with a restriction endonuclease. Any restriction endonuclease, or a combination thereof, may be used, however, it is preferred that the restriction endonuclease cleaves the DNA to produce as many smaller fragments as possible (but at least most fragments being 20 or more nucleotides in length), such as a restriction endonuclease that cleaves at a 4 base pair recognition sequence. Preferably; any fragments smaller than about 20 nucleotides in length are removed from the sample. This will minimize any non-specific hybridization events.

Although DNA from the second sample will typically comprise DNA fragments as a result of numerous factors including non-sequence specific endonucleases which act during cell death, the DNA from the second sample may also be cleaved with a suitable agent. In a preferred embodiment, the DNA in the second sample is cleaved with the same restriction enzyme(s) as the DNA in the first sample.

The DNA can be quantified using any technique known in the art. In one embodiment, the DNA is quantified through the use of an agent which binds the DNA. Preferably, the agent is picogreen. In some cases the agent may preferentially bind dsDNA. Thus, in these instances to ensure that the DNA quantified is dsDNA, the isolated DNA from viii) may be used as a template to synthesize a complementary strand thereto and the resulting dsDNA products quantified.

In another instance, a particularly preferred embodiment of the method of the ninth aspect comprises the following i) obtaining a first sample comprising maternal, but no or small quantities of fetal, DNA, ii) obtaining a second sample comprising fetal and maternal DNA, iii) denaturing the DNA obtained from i) and ii), iv) exposing the denatured DNA of the first and second samples in the same vessel to conditions which promote nucleic acid hybridization, and v) isolating and quantifying the DNA obtained from iv) which is derived from the second sample which has not hybridized to DNA from the first sample.

As the skilled addressee would be aware, numerous steps of this embodiment can be rearranged without altering the working of the invention. For example, i) could be performed after ii).

The DNA in the first sample of this embodiment is not only used to remove, at least partially, maternal DNA from the second sample but will also remove, at least partially, fetal DNA which has been inherited from the mother, as well as remove, at least partially, fetal DNA which has been inherited from the father which is the same or shares a high degree of sequence identity with DNA of the mother.

In a tenth aspect, the present invention provides a method of screening for a disease associated with abnormal levels of fetal DNA in the mother, the method comprising quantifying fetal DNA in a sample using a method of the ninth aspect.

Preferably, the disease is selected from, but not limited to, fetal trisomy 21, fetal trisomy 13, preterm labour, preeclampsia, and idiopathic polyhydramnios.

The present inventor has also devised a method for at least partially purifying fetal specific nucleic acids from a sample comprising fetal and maternal nucleic acids. This method relies, in part, on removing maternal DNA from the sample through nucleic hybridization procedures. Thus, in an eleventh aspect the present invention provides a method of enriching from a sample a DNA sequence which is present in fetal DNA but absent in maternal DNA, the method comprising;

i) obtaining a first sample comprising maternal, but no or small quantities of fetal, DNA, ii) obtaining a second sample comprising fetal and maternal DNA, iii) denaturing the DNA obtained from i) and ii), iv) exposing the denatured DNA of the first and second samples in the same vessel to conditions which promote nucleic acid hybridization, and v) collecting the non-hybridized DNA which is enriched in fetal specific DNA when compared to the second sample.

As used herein, the term "enriching" refers to the relative concentration (when compared to maternal DNA) of fetal specific DNA being increased compared to the relative concentration (when compared to maternal DNA) of fetal specific DNA in the second sample.

The enrichment aspect of the invention can be used in the methods of the invention related to the identification of fetal specific HLA alleles. However, the enrichment aspect may also be used to identify non-HLA markers of the fetal cells. Thus, in a twelfth aspect the present invention provides a method of identifying a DNA sequence which is present in fetal DNA but absent in maternal DNA, the method comprising;

i) obtaining a first sample comprising maternal, but no or small quantities of fetal, DNA, ii) obtaining a second sample comprising fetal and maternal DNA, iii) denaturing the DNA obtained from i) and ii), iv) mixing and exposing the denatured DNA of the first and second samples in the same vessel to conditions which promote nucleic acid hybridization, v) collecting the non-hybridized DNA which is enriched in fetal specific DNA when compared to the second sample, and vi) screening DNA from v) for non-maternal DNA sequences.

As the skilled addressee would be aware, numerous steps of this aspect can be rearranged without altering the working of the invention. For example, i) could be performed after ii).

The screening for non-maternal DNA as defined in step vi) can be performed by any technique known in the art. In one embodiment, the DNA from step v) is exposed to DNA amplification using primers directed to a locus of interest In an alternate embodiment, the DNA from step v) is placed on a solid support, such as used in microarray technology, and screened with allele specific probes for a locus of interest.

Preferably, the locus of interest is known to be polymorphic between individuals, such as loci of the HLA complex.

The method of the twelfth aspect can also be applied to RNA in a fetal cell which is differentially expressed when compared to a maternal cell. Thus, in a thirteenth aspect, the present invention provides a method of identifying an RNA sequence which is present in a fetal cell but absent in a maternal cell, the method comprising;

i) obtaining a first sample comprising maternal, but no or small quantities of fetal, RNA, ii) obtaining a second sample comprising fetal and maternal RNA, iii) reverse transcribing the RNA in the first and second samples to produce cDNA, iii) denaturing the cDNA obtained from iii), iv) mixing and exposing the denatured cDNA of the first and second samples in the same vessel to conditions which promote nucleic acid hybridization, v) collecting the non-hybridized cDNA which is enriched in fetal specific cDNA when compared to the second sample, and vi) screening cDNA from v) for sequences derived from fetal specific RNA.

Preferably, the term comprises "small quantities of fetal RNA" means that maternal RNA is found at least at a 100 fold, more preferably at least at a 1,000, and even more preferably at least at a 10,000 fold higher concentration than any contaminating fetal RNA.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting examples and with reference to the accompanying figures.

BRIEF DESCRIPTION OF THE ACCOMPANYING DRAWINGS

FIG. 1: HLA-A typing of maternal-cellular and plasma-derived DNA. Images show the results of reactions targeted to eight single types including A01, A02, A03, A11, A24, A26, A29 and A32. For each sample the left hand image indicates the types identified in maternal-cellular-derived DNA, while the right hand image identifies types found in plasma-derived DNA. HLA-A products are between 160 and 240 bp. The lane marked 'M' is a 100 bp DNA size ladder.

Figure 2:
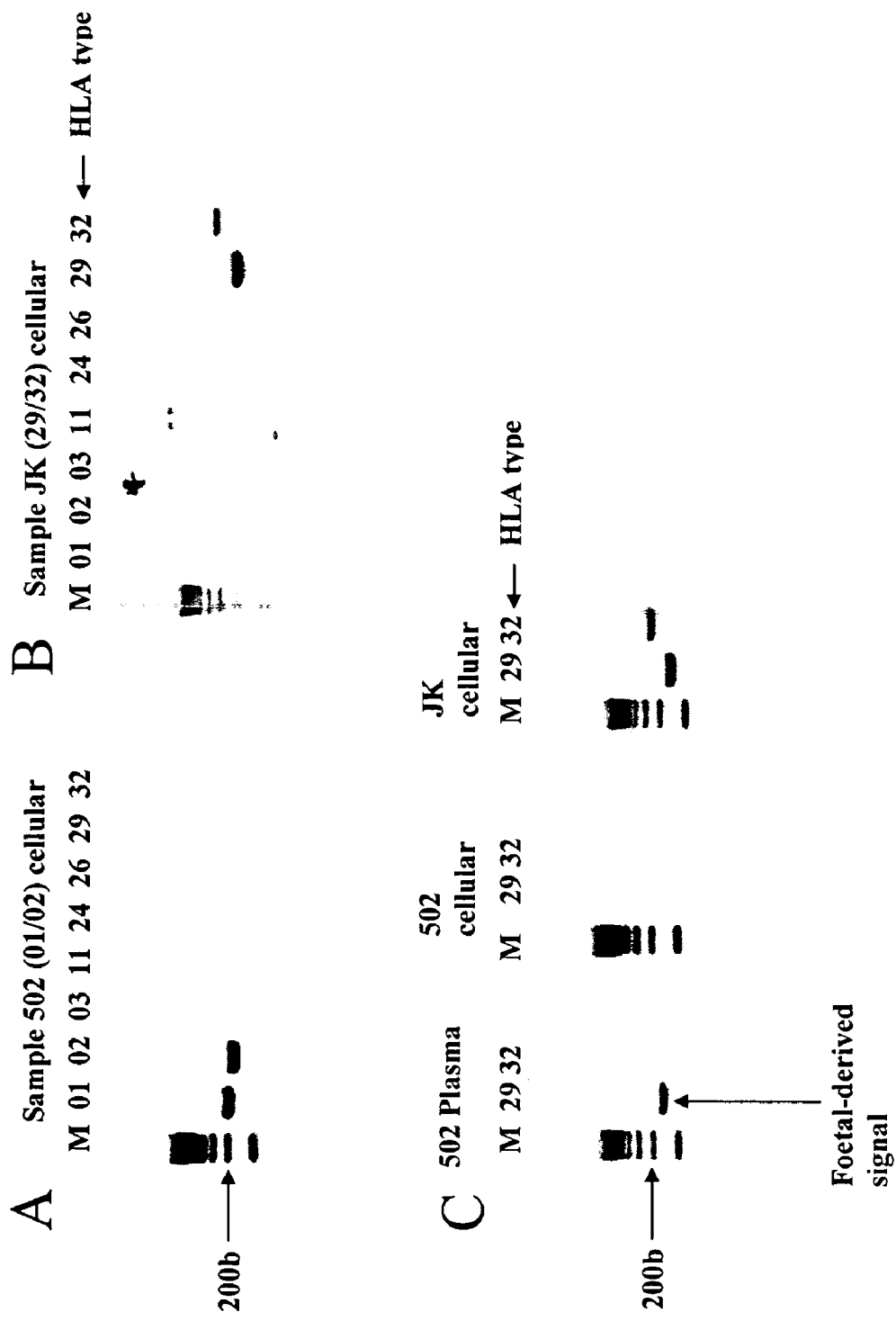

FIG. 2: HLA-A typing of maternal-cellular, paternal-cellular and maternal plasma-derived DNA. Panels A & B show the results of reactions targeted to eight single types including A01, A02, A03, A11, A24, A26, A29 and A32. Panel A shows typing of maternal DNA (sample 502). Panel B shows typing of paternal DNA (sample JK). Panel C shows reactions targeted to the paternal types (A29/A32) using plasma-derived DNA, maternal DNA and paternal DNA. HLA-A products are between 160 and 240 bp. The lane marked 'M' is a size ladder.

DETAILED DESCRIPTION OF THE INVENTION

General Techniques

Unless defined otherwise, all technical and scientific terms used herein have the same meaning as commonly understood by one of ordinary skill in the art (e.g., in cell culture, molecular genetics, immunology, nucleic acid chemistry, hybridization techniques and biochemistry).

Unless otherwise indicated, the recombinant DNA and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the term "high stringency conditions" for hybridization refers to, but is not limited to, conditions such as 50% formamide, 6×SSC at 42° C. (or other similar hybridization solution), followed by washing conditions of about 60-68° C., in 0.2×SSC, 0.1% SDS (see Sambrook et al. (1989) and Ausubel et al. (1988) supra).

As used herein, the term "fetal specific" or variations thereof merely refers to an allele or protein which is possessed by a fetus of a pregnant female but said allele or protein is does form part of (not encoded by in the case of proteins) the mothers genome.

Genotyping/Typing

The locus (loci) analysed using the methods of the first or second aspect can be any locus (loci) known to be, or determined to be, polymorphic between different members of a population. Examples of such polymorphic loci are well known in the art. In some cases the polymorphic loci are linked to a disease state, however, in many instances the polymorphic loci are not linked to a disease state. In one embodiment, the polymorphism is a single nucleotide polymorphism (SNP). Examples of SNPs that could be alleles targeted by the methods of the invention to identify a fetal specific nucleic acid in a pregnant female are provided in many sources including databases that are available at ncbi.com.

Alleles at a given locus can be detected using any method known in the art, including PCR, nucleic acid sequencing and antibody detection systems, generally described below in relation to typing HLA alleles.

HLA Typing

HLA typing can be performed using any technique known in the art. A general overview of such procedures is provided in Parham et al. (1999), Gerlach (2002), as well as Hui and Bidwell (1993). These techniques include serological and molecular typing, or a combination thereof, procedures. The mother can be typed using any procedure, although molecular typing procedures are generally replacing the use of serological techniques. In contrast, as the fetal material to be analysed is nucleic acid the typing procedures in this instance will be using nucleic acid detection based techniques.

There are many commercial suppliers of "kits" and/or reagents for HLA typing. These include, but are not limited to, Dynal Biotech (Oslo, Norway), Pel-Freez Clinical Systems, LLC (Wisconsin, USA), Biotest (Frankfurt, Germany), Forensic Analytical (California, USA), and Innogenetics (Gent, Belgium). Such kits and/or reagents can be used in the methods of the invention.

An example of a standard procedure used for serological HLA typing is the lymphocyte microcytoxicity assay (Hui and Bidwell, 1993) which is also known the art as complement-dependent cytotoxicity assay. In such an assay anti-HLA serum, or monoclonal antibody, is mixed with live lymphocytes obtained from the mother. Specific Ig binds to the polymorphic protein moiety of the HLA molecule expressed on the cell surface. Exogenous complement is added to the well which will result in lysis of cells to which antibody has been bound. Cell death is determined by, for example, ethidium bromide vital stain exclusion. Specific binding is detected by, for example, vital dye stain. Vital dye exclusion techniques, which are commonly used, often require millions of viable lymphocytes that express HLA antigens which makes them difficult to perform in small children or patients with low white cell counts. Accordingly, the small number of fetal cells which may be in a sample obtained from the maternal blood will not influence the correct HLA typing of the mother using this procedure.

Many methods based on nucleic acid amplification are currently used for the detection of HLA alleles (Mike et al., 1997). Such molecular techniques can be catergorised into at least four types: i) methods that generate a product containing internally located polymorphisms that are identified by a second technique (for example, sequence specific oligonucleotide probes (SSOP)); ii) methods in which the polymorphism is identified directly as part of the PCR process although there are post-amplification steps (for example the use of sequence specific primers); iii) methods which analyse different mutations generating specific conformation changes (heteroduplexes), and iv) methods that rely on DNA sequencing. The choice of method in a laboratory will depend on a number of factors including, but not limited to, clinical urgency, resolution, sample numbers, budget, equipment availability, and staff skills.

Amplification of DNA followed by probing with sequence-specific oligonucleotide probes (SSOP) can be performed using several related procedures. The principle of this approach is that different alleles at a locus can be detected by probes recognizing the allelic differences and used to detect the complementary region of an amplified target. It is customary to have one of the DNA strands in the reaction immobilized. However, procedures where both immobilization of the target and the probe motifs have been developed. If the amplified product is immobilized, then the probe is labeled and applied. This is a traditional dot blot, named such because the target is spotted as dots on a filter or membrane. The material can also be applied as a line, and the process is then referred to as a slot blot. If the probe is immobilized and the amplified target is labeled, the assay is then referred to as a reverse dot blot or a "blot dot." These methods are well suited to high-throughput needs, as many samples can be spotted and probed in a single reaction in the dot-blot scenario, and a sample can be reacted with many probes in one reaction in a blot-dot paradigm. To use many probes at once, the temperature of melting for the probes needs to be optimized.

Amplification of an allele at a locus using allele-specific primers is also used extensively. This method is often referred to as sequence-specific primer (SSP) or amplification refractory mutation system (ARMS) typing. While SSP and ARMS have a slightly different context, the principle is very much the same. In these systems, the amplification process is performed using one primer that is conserved across many alleles and a second primer specific for a single nucleotide polymorphism. The 3' end of a primer must be firmly bound to the target for the polymerase to extend the strand. The detection employed in SSP or ARMS methods is usually an agarose gel fractionation of products. Most kits available have multiple primer sets in separate reactions to type for many alleles at a locus or loci. Temperature of melting optimization of the primers is necessary to allow thermal cycling of all reactions in a single instrument. Testing using SSP and ARMS can yield low-, medium-, or high-resolution results, depending on the primer sets used.

Given the proper physical environment, DNA will form secondary structures. The placement of the "loops" and "hairpins" that form are sequence dependent. If 2 alleles have different sequences, the types and placement of secondary structures should differ. This is the basis of double-stranded sequence conformation polymorphism testing. The concept is that alleles allowed to form secondary structures can be discriminated among themselves by the migration of these secondary structures in a gel matrix environment. Resolution can be enhanced by utilizing a reference strand in the duplex formations. This serves as an internal reference across all allele combinations, because only those duplexes with the reference strand are visualized.

The advent of capillary sequencers has made HLA typing by sequencing more economical and gives a quicker and larger throughput than previous sequencing technologies.

In the future many of the techniques now evolving to ascertain single nucleotide polymorphisms (SNP) will be applied in the HLA field e.g. wave technology, mass spectrometry, and microarrays. Furthermore, many methods will become automated.

As outlined above, it is preferred that screening the nucleic acids from the sample for at least one HLA allele targets HLA alleles which are common in the population but absent in the mother. Naturally, this reduces the number of alleles which need to be analysed before a fetal DNA/cell marker is identified. Preferably, the targeted HLA allele is found within at least 5%, more preferably 10% of the population. Information regarding known HLA alleles, as well as their frequency within the population, can be determined using standard typing procedures, the results of which have been widely reported (see, for example, Middleton et al. (2000); Williams et al. (2002); Marsh et al. 2002; Robinson et al., 2003; Middleton et al., 2002).

Fetal DNA Isolation and Analysis Thereof

Fetal DNA can be obtained from the sample using any-technique known in the art. Preferably, the sample is maternal plasma or serum obtained during the first trimester of pregnancy. A review of fetal DNA in maternal plasma and serum is provided by Pertl and Bianchi (2001), as well as Lo (2000).

As outlined in WO 98/39474, maternal plasma can be obtained from whole maternal blood by separating the cellular fraction through centrifugation at 3000 g. Following centrifugation the plasma layer is removed and placed into a polypropylene tube containing an anti-coagulant such as EDTA. Although DNA can be extracted from the plasma sample using standard techniques involving, for example ethanol precipitation or affinity column purification (such as those produced by Qiagen, Calif., USA), molecular analysis such as nucleic acid amplification can be performed essentially directly on the plasma or serum sample.

Molecular techniques for the analysis of fetal nucleic acids are the essentially same as the molecular techniques described above in the HLA typing section. As outlined in Hahn et al. (2001), the TaqMan system (Applied Biosystems, California, USA) has shown to provide robust and reproducible results.

Nucleic Acid Quantification

Nucleic acids identified/isolated using methods of the invention can be quantitated using any technique known in the art.

In one embodiment, upon the identification of a fetal specific allele which is not present in the mother a quantitative polymerase chain reaction (QPCR) can be performed, for example on a maternal plasma or serum sample, to determine the relative quantity of the allele in the sample. This in turn can be used as a marker for diseases such as fetal trisomy 21.

QPCR is a method for quantifying a nucleic acid molecule based on detection of a fluorescent signal produced during PCR amplification (Gibson et al., 1996). Amplification is carried out on machines such as the PRISM 7700 detection system (ABI) which consists of a 96-well thermal cycler connected to a laser and charge-coupled device (CCD) optics system. To perform QPCR, a PCR reaction is carried out in the presence of a doubly labeled probe. The probe, which is designed to anneal between the standard forward and reverse PCR primers, is labeled at the 5' end by a fluorogenic reporter dye such as 6-carboxyfluorescein (6-FAM) and at the 3' end by a quencher molecule such as 6-carboxy-tetramethyl-rhodamine (TAMRA). As long as the probe is intact, the 3' quencher extinguishes fluorescence by the 5' reporter. However, during each primer extension cycle, the annealed probe is degraded as a result of the intrinsic 5' to 3' nuclease activity of Taq polymerase. This degradation separates the reporter from the quencher, and fluorescence is detected every few seconds by the CCD. The higher the starting copy number of the nucleic acid, the sooner an increase in fluorescence is observed. A cycle threshold (CT) value, representing the cycle number at which the PCR product crosses a fixed threshold of detection is determined by the instrument software. The CT is inversely proportional to the copy number of the template and can therefore be used to calculate either the relative or absolute initial concentration of the nucleic acid molecule in the sample. The relative concentration of two different molecules can be calculated by determining their respective CT values (comparative CT method). Alternatively, the absolute concentration of the nucleic acid molecule can be calculated by constructing a standard curve using a housekeeping molecule of known concentration. The process of calculating CT values, preparing a standard curve, and determining starting copy number can be performed using SEQUENCE DETECTOR 1.7 software (ABI).

Examples of QPCR procedures which are useful for the present invention include, but are not limited to, those generally described by Honda et al. (2002), Lo et al. (1999), Lee et al. (2002), Wataganara et al. (2003), and Zhong et al. (2000).

Nucleic acids may also be quantified by using agents which bind thereto. Examples of such agents include, but are not limited to, ethidium bromide, Hoechst 33258 and picogreen. In a preferred embodiment, the agent is picogreen (Ahn et al., 1996).

In another embodiment the nucleic acids are quantified using an antibody which is specific therefor but which binds independent of the actual nucleotide sequence. An example of an antibody which is specific for, and can be used to quantify, ssDNA is described by Batova et al. (1993).

In a further embodiment, particularly with regard to DNA obtained from the method of the ninth aspect, the DNA can be quantified by ligating adapter fragments to the end of the DNA and using primers directed against the adapters to amplify the ligated DNA in a QPCR procedure (see, for example, Zou et al., 2003).

Fetal Cell Isolation

At least some fetal cell types such as platelets, trophoplasts, erythrocytes and leucocytes have been shown to cross the placenta and circulate in maternal blood (Douglas et al., 1959; Schroder, 1975). Such fetal cells can provide fetal DNA for prenatal genetic testing. Fetal cell isolation requires a unique marker for fetal cells, which are present in maternal blood at a frequency of less than 1 fetal cell in 1,000,000 maternal cells.

The identification of a fetal cell marker by the methods of the invention can be used to assist in fetal cell isolation. Methods are available for selecting cells using markers which are either inside the cell or on the cell surface. In a preferred embodiment, the fetal cell marker is localised on the cell surface. In particular, as with numerous aspects of the present invention, the fetal cell marker is an HLA antigen.

Preferably, the sample comprising fetal cells is obtained from a pregnant woman in her first trimester of pregnancy. In one embodiment the sample can be a blood sample which is prevented from clotting such as a sample containing heparin or, preferably, ACD solution. The sample is preferably stored at 0 to 4° C. until use to minimize the number of dead cells, cell debris and cell clumps. The number of fetal cells in the sample varies depending on factors including the age of the fetus. Typically, from 7 to 20 ml of maternal blood provides sufficient fetal cells upon separation from maternal cells. Preferably, 30 ml or more blood is drawn to ensure sufficient cells without the need to draw an additional sample.

In another embodiment, the fetal cells are obtained from the cervical mucous of the mother as, for example, generally described in WO 03/020986.

Before being selected using a method of the invention, the fetal cells may at least be partially purified from a sample obtained from the mother by a procedure such as that described in WO 03/102595.

A fetal cell specific affinity reagent is used to isolate fetal cells away from maternal cells present in the central maternal blood sample. Isolation may be accomplished by a variety of techniques well known in the art, including cell sorting, especially fluorescence-activated cell sorting (FACS), by using an affinity reagent bound to a substrate (e.g., a plastic surface, as in panning), or by using an affinity reagent bound to a solid phase particle which can be isolated on the basis of the properties of the beads (e.g., colored latex beads or magnetic particles). As will be apparent to one of skill in the art, the fetal cell affinity reagent may be bound directly or indirectly (e.g., via a secondary antibody) to the dye, substrate, or particle. In a particularly preferred embodiment, the fetal cell affinity reagent is an antibody that binds a HLA antigen of the fetal cell, wherein the maternal cells do not express the antigen.

For isolation of fetal cells by cell sorting, the affinity reagent is labeled directly or indirectly with substance which can be detected by a cell sorter, preferably a dye. Preferably, the dye is a fluorescent dye. A large number of different dyes are known in the art, including fluorescein, rhodamine, Texas red, phycoerythrin, and the like. Any detectable substance which has the appropriate characteristics for the cell sorter may be used (e.g., in the case of a fluorescent dye, a dye which can be excited by the sorter's light source, and an emission spectra which can be detected by the cell sorter's detectors).

For isolation of fetal cells using solid-phase particles, any particle with the desired properties may be utilized. For example, large particles (e.g., greater than about 90-100 μm in diameter) may be used to facilitate sedimentation. Preferably, the particles are "magnetic particles" (i.e., particles which can be collected using a magnetic field). Magnetic particles are now commonly available from a variety of manufacturers including Dynal Biotech (Oslo, Norway). An example of magnetic cell sorting (MACS) is provided by Al-Mufti et al. (1999).

When a dye or a solid phase particle is used in conjunction with the affinity reagent to isolate fetal cells from the central maternal blood sample, the dye or solid phase particle may be directly or indirectly linked to the affinity reagent. Whether the affinity reagent is directly or indirectly linked is left to the discretion of the practitioner. Directly labeled affinity reagents are produced by linking the dye or solid phase particle to the affinity reagent by, for example, covalent linkage of a dye or by adsorption to a solid phase particle. Affinity reagents may be indirectly labeled using a variety of methods known in the art; such as using a "secondary antibody" (a directly labeled antibody which binds specifically to the affinity reagent), or by exploiting a binding pair such as biotin and streptavidin (e.g., by derivatizing the affinity reagent with biotin, and using directly labeled streptavidin to bind label to the affinity reagent).

For isolation of fetal cells using an affinity reagent bound to a substrate, the affinity reagent is preferably adsorbed or bound directly to the substrate. Preferably, the substrate is the surface of a plastic plate or flask, and the affinity reagent is directly adsorbed to the surface. Adsorption is easily accomplished for most affinity reagents, and when the affinity reagent is an antibody, adsorption is accomplished by simply incubating a solution containing the antibody on the substrate. Alternately, a modified substrate may be used, such as a substrate modified with avidin or streptavidin, and an affinity reagent modified with biotin, or an amine-derivatized substrate activated with a bifunctional crosslinking agent. Preferably, the affinity reagent is adsorbed to the substrate by incubating a solution containing the affinity reagent on the substrate.

Fetal cell isolation may be aided by the depletion of maternal cells prior to fetal cell sorting. In this case the mononuclear cell layer can be initially isolated from the blood of pregnant women by centrifugation. The resulting cell suspension consists predominantly of maternal cells; in order to enrich the eventual proportion of fetal cells present, the maternal cells are selectively removed by incubating the cells with antibodies attached to a solid support. Such supports include magnetic beads, plastic flasks, plastic dishes and columns. The antibodies bind antigens present on the cell surface of mature leukocytes. Thus, a non-trivial number of maternal leukocytes are eliminated by virtue of being bound to the solid support. The total number of cells remaining in the cell suspension is smaller, but the proportion of fetal cells present is larger.

As outlined above, preferably the affinity reagent is an antibody or fragment or derivative thereof.

Monoclonal antibodies which will bind to HLA antigens are already known but in any case, with today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982).

Polyclonal antibodies are useful in the methods of the invention. Monospecific polyclonal antibodies are preferred. Suitable polyclonal antibodies can be prepared using methods well known in the art.

Fragments of antibodies, such as Fab and Fab$_2$ fragments may also be used as can genetically engineered antibodies and antibody fragments.

The variable heavy ($V_H$) and variable light ($V_L$) domains of the antibody are involved in antigen recognition. Variable domains of rodent origin may be fused ("humanized") to constant domains of human origin such that the resultant antibody retains the antigenic specificity of the rodent parented antibody.

That antigenic specificity is conferred by variable domains and is independent of the constant domains is known from experiments involving the bacterial expression of antibody fragments, all containing one or more variable domains. These molecules include Fab-like molecules; Fv molecules; single-chain Fv (ScFv) molecules where the $V_H$ and $V_L$ partner domains are linked via a flexible oligopeptide, and single domain antibodies (dAbs) comprising isolated V domains.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent") By "bivalent" we mean that the said antibodies and F(ab')$_2$ fragments have two antigen combining sites. In contrast, Fab, Fv, ScFv and dAb fragments are monovalent, having only one antigen combining site.

After isolation using the affinity reagent, the isolated fetal cells may be used directly for prenatal genetic testing, or they may be cultured to expand cells numbers and to facilitate karyotypic analysis.

Uses

Numerous conditions have been linked to abnormal amounts of fetal DNA in maternal blood, such conditions include, but are not limited to, fetal trisomy 21 (Down syndrome) (Lee et al., 2002), fetal trisomy 13 (Wataganara et al., 2003), preterm labour (Leung et al., 1998), preeclampsia (Lo et al., 1999), and idiopathic polyhydramnios (Zhong et al., 2000) (for a review see Pertl and Bianchi, 2001). Gender-independent fetal DNA markers identified by the methods of the present invention can be used to quantify fetal DNA in, for example, the plasma/serum of a mother to detect conditions/diseases, such as those outlined above, associated with abnormal levels of fetal DNA.

In addition, the fetal cell markers identified by the methods of the present invention can be used to isolate fetal cells. For example, antibodies which bind HLA antigens which are fetal specific (i.e. determined by the methods of the invention to be specific for a given fetus when compared to the maternal HLA type) can be used in, for example, flow cytometry procedures to isolate fetal cells. Because such isolated fetal cells comprise the same genetic DNA make up of the somatic cells of the fetus, these isolated fetal cells can be analysed for abnormalities using techniques known in the art. Such analysis can be performed on any cellular material that enables defects to be detected. Preferably, this material is nuclear DNA, however, at least is some instances it may be informative to analyse RNA or protein from the isolated fetal cells. Furthermore, the DNA may encode a gene, or may encode a functional RNA which is not translated, or the DNA analysed may even be an informative non-transcribed marker.

In one preferred embodiment, chromosomal abnormalities are detected. By "chromosomal abnormality" we include any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome which can be detected by DNA analysis.

Other genetic disorders which can be detected by DNA analysis are known such as 21-hydroxylase deficiency or holocarboxylase synthetase deficiency, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 7th Edition, Volumes I, II and III, Scriver, C. R., Beaudet, A. L., Sly, W. S., and Valle, D. (eds), McGraw Hill, 1995. Clearly, any genetic disease where the gene has been cloned and mutations detected can be analysed.

Genetic assay methods include the standard techniques of karyotyping, analysis of methylation patterns, restriction fragment length polymorphism assays and PCR-based assays, as well as other methods described below.

Chromsomal abnormalities can be detected by karyotyping which is well known in the art. Karyotyping analysis is generally performed on cells which have been arrested during mitosis by the addition of a mitotic spindle inhibitor such as colchicine. Preferably, a Giemsa-stained chromosome spread is prepared, allowing analysis of chromosome number as well as detection of chromosomal translocations.

The genetic assays may involve any suitable method for identifying mutations or polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denating gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, ie capable of detecting a mutation at another position or gene which is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

Amplification of DNA may be achieved by the established PCR methods or by developments thereof or alternatives such as the ligase chain reaction, QB replicase and nucleic acid sequence-based amplification.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which hybridise to either the wild-type genotype or the mutant genotype but not both. Whether amplified DNA is produced will then indicate the wild-type or mutant genotype (and hence phenotype).

A preferable method employs similar PCR primers but, as well as hybridising to only one of the wild-type or mutant sequences, they introduce a restriction site which is not otherwise there in either the wild-type or mutant sequences.

In order to facilitate subsequent cloning of amplified sequences, primers may have restriction enzyme sites appended to their 5' ends. Thus, all nucleotides of the primers are derived from the gene sequence of interest or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available.

PCR techniques that utilize fluorescent dyes may also be used to detect genetic defects in DNA from fetal cells isolated by the methods of the invention. These include, but are not limited to, the following five techniques.

i) Fluorescent dyes can be used to detect specific PCR amplified double stranded DNA product (e.g. ethidium bromide, or SYBR Green I).

ii) The 5' nuclease (TaqMan) assay can be used which utilizes a specially constructed primer whose fluorescence is quenched until it is released by the nuclease activity of the Taq DNA polymerase during extension of the PCR product.

iii) Assays based on Molecular Beacon technology can be used which rely on a specially constructed oligonucleotide that when self-hybridized quenches fluorescence (fluorescent dye and quencher molecule are adjacent). Upon hybridization to a specific amplified PCR product, fluorescence is increased due to separation of the quencher from the fluorescent molecule.

iv) Assays based on Amplifluor (Intergen) technology can be used which utilize specially prepared primers, where again fluorescence is quenched due to self-hybridization. In this case, fluorescence is released during PCR amplification by extension through the primer sequence, which results in the separation of fluorescent and quencher molecules.

v) Assays that rely on an increase in fluorescence resonance energy transfer can be used which utilize two specially designed adjacent primers, which have different fluorochromes on their ends. When these primers anneal to a specific PCR amplified product, the two fluorochromes are brought together. The excitation of one fluorochrome results in an increase in fluorescence of the other fluorochrome.

Fetal cells have been found to persist for decades postpartum, and are capable of further differentiation and migration into maternal organs. As a result, the mother can be considered as a chimera (for a review see Bianchi et al. 2000). This phenomenon has been associated with various diseases, particularly autoimmune type diseases. Such diseases associated with feto-maternal cell-trafficking and/or microchimerism (for example scleroderma) can also be analysed using the methods of the present. More specifically, the fetal cell specific markers identified by the methods of the invention can be used to locate, quantify, capture and/or characterize fetal cells in the mother following birth or loss of the fetus.

EXAMPLES

Example 1

Materials and Methods
Isolation of DNA from Plasma
Preparation of Cell-Free Plasma from Whole Blood
1. Centrifuge whole blood at 1000×g for 10 minutes
2. Allow cells to settle for a further 10 minutes
3. Remove plasma phase with a pipette
4. Re-centrifuge the plasma phase at 1600×g for 10 minutes
5. Aliquot plasma into 1.5 ml Eppendorf tubes
6. Centrifuge at 16000×g for 5 minutes
7. Transfer cleared plasma to a clean tube for DNA extraction or storage.

DNA Extraction

Genomic DNA was extracted from 200 µl of plasma using the Qiagen QIAmp DNA Blood minikit, following the Blood and Body Fluids protocol with the following modifications. The DNA solution was passed through a single column four (4) consecutive times before the wash steps. DNA was eluted from the column using 65 µl of warm (56° C.) 1×PCR buffer (Invitrogen). The eluate was re-loaded onto the column for a second elution. Multiple extractions (200 µl per column) from the same plasma sample were pooled for use in the HLA-A PCR reactions.

A detailed protocol follows:
1. Add 200 µl Plasma to a 1.5 ml tube
2. Add 200 µl of Qiagen Protease (or proteinase K)
3. Add 200 µl of Qiagen buffer AL
4. Incubate at 56° C. for 10-30 minutes
5. Add 200 µl 100% Ethanol and mix well
6. Apply to a Qiagen QIAmp DNA Blood Minikit column and spin at 3000 rpm for 1 minute
7. Re-apply the eluate to the same column and spin at 300 rpm for 1 minute
8. Repeat step 7. twice more (i.e., a total of four passes through the column)
9. Place column in a fresh collection tube and add 500 µl of Qiagen buffer AW1 then spin at full speed for 1 minute
10. Place column in a fresh collection tube and add 500 µl of Qiagen buffer AW2 then spin at full speed for 1 minute
11. Empty collection tube and re-spin column at full speed for 2 minutes to dry
12. Add 65 µl of Qiagen elution buffer (pre-warmed to 56° C.), allow to sit for at least 1 minute and spin at full speed for 1 minute
13. Eluants from multiple 200 µl aliquots of a single plasma sample, processed with separate columns, are added back onto each column for a final elution, and then pooled.
14. Store DNA at −20° C.
15. 20 µl aliquots of the pooled DNA solution are to be entered into the targeted PCR reactions.

Extraction of DNA from Whole Blood

Genomic cellular DNA is extracted from 200 µl of whole blood using the Qiagen QIAamp DNA Blood minikit according to the manufacturers instructions and including two 100 µl elution's in warm (56° C.) elution buffer. Detailed protocol is as follows:
1. Add 200 µl of whole blood to a 1.5 ml eppendorf tube
2. Add 20 µl of Qiagen Protease (or proteinase K)
3. Add 200 µl of Qiagen buffer AL 4. Incubate at 56° C. for 10-30 minutes
5. Add 200 μl 100% Ethanol and mix well
6. Apply to a Qiagen QIAmp DNA Blood Minikit column and spin at 6000 rpm for 1 minute
7. Place column in a fresh collection tube and add 500 μl of Qiagen buffer AW1 then spin at full speed for 1 minute
8. Place column in a fresh collection tube and add 500 μl of Qiagen buffer AW2 then spin at full speed for 1 minute
9. Empty collection tube and re-spin column at full speed for 2 minutes to dry
10. Add 100 μl of Qiagen buffer EB (pre-warmed to 56° C.), allow to sit for at least 1 minute and spin at full speed for 1 minute
11. Add eluate back onto the column, allow to sit for at least 1 minute and spin at full speed for 1 minute
12. Quantitate DNA by reading OD260 on an Eppendorf Biophotometer with a programmed factor of 1 OD260=50 μg/ml dsDNA
13. Store eluted DNA at −20° C.

Amplification of HLA-A Specific Sequences

HLA-A specific sequences were amplified from cell-derived genomic DNA or plasma-derived DNA according to the following protocol.

1. Amplification reactions were carried out in a total volume of 25 μl
2. Each reaction contained the following components
   1 ng of cellular-derived genomic DNA or 10-20 μl of plasma-derived DNA
   12.5 pmoles of each primer
   1×PCR buffer (Invitrogen) i.e: 20 mM Tris-HCl (pH 8.4), 50 mM KCl, 1.0 mM MgCl$_2$ (final concentrations)
   200 μM dNTPs
   HotStar Taq (0.625 units) (Qiagen GmbH, Germany)
3. Cycling was performed on a Corbett Research Palm cycler with an initial denaturation step of 95° C. for 15 minutes followed by 45 cycles of 95° C. for 20 seconds, 62° C. or 66° C. (see 4.) for 30 seconds and 72° C. for 20 seconds. A final extension step was carried out at 72° C. for 2 minutes before cooling to ambient temperature.
4. Reactions targeting HLA-A A1, A2 and A3 were carried out with an annealing temperature of 66° C. All other HLA targeted reactions had an annealing temperature of 62° C.

Analysis of Amplification Products

Following thermo-cycling, a 10 μl aliquot from each of the reactions was analysed by electrophoresis through a 2.5% agarose gel in 0.5×TBE buffer. The gel was stained with a DNA-binding fluorescent dye, and results visualised by trasillumination and photographed with a CCD camera.

Product sizes were compared to a 100 bp Molecular Ruler (Biorad, Hercules, Calif., USA) to determine if the correct sized product was formed.

HLA-A Testing of Maternal Cell-Derived DNA by Commercial Methods

All maternal blood cell samples (and a single paternal sample) were HLA-A tested using at least one commercially available product and protocol. Two products were available; the Olerup SSP™ HLA-A Low Resolution kit (Olerup SSP AB, Sweden) and LifeMATCH™ DNA typingkit with Quick-Types software, version 27, (Orchid Diagnostics, Stamford, Conn.), analysed by a Luminex multiplex bead analyser (Luminex, Austin, Tex.). In each case reactions were carried out according to the manufacturers instructions.

Design and Testing of HLA-Type Specific PCR Primers

Oligonucleotide primer pairs were designed for the individual PCR amplification of HLA-A type-specific sequences (Table 1). Primers were designed manually using an alignment of all described HLA-A sequences obtained from the IMGT/HLA database.

Primers were tested for optimal annealing temperature and specificity using an annealing gradient in PCR. This involved testing each primer pair against a template containing the specific HLA-A type targeted and, in a separate reaction, a template containing a non-specific HLA-A type. An annealing temperature for specific type reaction was chosen when a strong product was observed for the template containing the specific type and no product was observed for the template containing the non-specific type. Initial gradient reactions were carried out in a final concentration of 1.5 mM MgCl$_2$. Once a suitable annealing temperature had been chosen primer pair specificity was further optimised by altering MgCl$_2$ concentrations at which point 1 mM MgCl$_2$ was determined as the most suitable concentration to be used will all primer sets.

The primers identified and tested for the examples fell into two groups with identical optimal PCR reaction conditions, so that they can also be used in multiplex reactions, permitting the search of fetal-specific HLA sequences in only 2 reactions, followed by amplicon identification on the basis of different amplicon lengths. (This procedure necessitates the use of labelled primers). Further primer design and testing will make it possible to search for most HLA sequences using a single multiplex reaction.

Results and Discussion

The results of screening experiments, designed to identify fetal HLA-A type from maternal plasma, are shown in FIGS. 1 and 2. In each case, the maternal HLA-A type was initially determined by a commercially available method (Olerup or Luminex). Then a panel of eight HLA-A type-specific primer pairs was used to screen both maternal cell-derived DNA and plasma-derived DNA. This panel included HLA-A types A01, A02, A03, A11, A24, A26, A29 and A32, giving population coverage of approximately 84% (Table 1).

TABLE 1

Oligonucleotide primer sequences used in the detection of specific HLA-A types. The population frequency figures are as reported in ashi-hla.org/ publicationfiles/archives/prepr/mori_qf.htm

| HLA-A type targeted | Population frequency | Oligonucleotide name | Oligonucleotide sequence | Expected product size |
|---|---|---|---|---|
| A1 | 15.18 | A1Fcv1 | TGTATGGCTGCGACGT GGGGC (SEQ ID NO:1) | 221 exon3 |
| | | A1Rv3s2 | CAGGTATCTGCGGAGC CCG (SEQ ID NO:2) | |
| A2 | 28.65 | A2Fv3s2 | GGAGCCCCGCTTCATC GCA (SEQ ID NO:3) | 188 exon2 |
| | | A2Rv3s2 | CGCAGGGTCCCCAGGT CCA (SEQ ID NO:4) | |
| A3 | 13.39 | A3Fv2s | ATGGCTGCGACGTGGG GT (SEQ ID NO:5) | 2-3 exon3 |
| | | A3Rv3s2 | CCACTCCACGCACGTG CCA (SEQ ID NO:6) | |

TABLE 1-continued

Oligonucleotide primer sequences used in the detection of specific HLA-A types. The population frequency figures are as reported in ashi-hla. org/ publicationfiles/archives/prepr/mori_qf.htm

| HLA-A type targeted | Population frequency | Oligonucleotide name | Oligonucleotide sequence | Expected product size |
|---|---|---|---|---|
| A11 | 6.17 | A1Fcv3s2 | TATGGCTGCGACGTGG GGC (SEQ ID NO:7) | 188 Exon3 |
|  |  | A11Rv2s | CCTCCAGGTAGGCTCT CT (SEQ ID NO:8) |  |
| A24 | 9.32 | A24Fv3s2 | ACACCCTCCAGATGAT GTT (SEQ ID NO:9) | 204 exon3 |
|  |  | A24Rv3s2 | CCCTCCAGGTAGGCTC TCT (SEQ ID NO:10) |  |
| A26 | 3.88 | A26Fcv1 | TCCATGAGGTATTTCT ACACC (SEQ ID NO:11) | 216 exon2 |
|  |  | A26Rv2s | GCAGGGTCCCCAGGTT CG (SEQ ID NO:12) |  |
| A29 | 3.58 | A29Fcv1 | CCCACTCCATGAGGTA TTTCA (SEQ ID NO:13) | 138 exon2 |
|  |  | A29Rv3s2 | CTCCTGCTCTATCCAC GGT (SEQ ID NO:14) |  |
| A32 | 3.70 | A32Fcv1 | CCACTCCATGAGGTAT TTCTT (SEQ ID NO:15) | 233 exon2 |
|  |  | A25Rcv2s | GTAGCGGACCGCGATC CG (SEQ ID NO:16) |  |

Although the maternal HLA-A type had been determined using commercially available methods the cellular-derived DNA was included to test for any non-specific amplification. (Maternal blood contains only less than 1 fetal cell per 1 million maternal cells, so that the contamination of maternal DNA with fetal DNA in cell-derived DNA is too small to result in a fetal-specific signal. This is in contrast to cell-free plasma DNA which contains typically >5% fetal DNA). An example of such non-specific amplification can be seen in sample 33 (FIG. 1), where the primer pair directed at A03 is non-specifically amplifying a target in the maternal A02/A30 sample. As the A03 product appears in both the cellular and plasma-derived DNA samples it can be excluded as a fetal-specific type. The plasma-derived DNA from sample 59 also shows a non-specific product produced by the A03 primer pair. This product is weak and we have noted occasional cross-reactivity with the A03 primer pairs in the past (as noted above for sample 33). Regardless, HLA-A03, and other, allele specific primers which do not result in any non-specific products can readily be designed and tested using routine techniques well within the capacity of the skilled addressee.

Each of the examples presented in FIG. 1 shows a clear, strong band that is unique to the plasma-derived DNA sample and thus is predicted to be of fetal origin. For sample 33 the unique foetal signal is HLA-A01, for sample 59 the unique fetal signal is HLA-A24 and for sample 69 the unique foetal signal is HLA-A29.

Paternal DNA was available in only one sample. The knowledge of paternal HLA-A type allowed us to confirm the results by specifically targeting these types in the maternal plasma-derived DNA sample and the results of this experiment are shown in FIG. 2. It can be seen in panels A & B that the primer panel is correctly predicting maternal and paternal HLA-A type. Panel C shows the targeted reactions and included maternal, paternal and plasma-derived DNA. A single, strong, HLA-A29 signal is visible in the plasma sample indicating that this allele has been inherited by the foetus from the father.

Example 2 (Prophetic)

A lymphocyte preparation is obtained form a pregnant female and HLA typed using HLA serological typing trays obtained from Pel-Freez Clinical Systems, LLC (Wisconsin, USA).

A list of HLA alleles which the mother does not possess is prepared. Preferably, the list is ordered to ensure that the more common HLA alleles are tested first. This will reduce costs, as less HLA alleles should need to be screened before a HLA antigen specific to the fetal cells is identified.

A maternal plasma sample comprising fetal DNA is prepared as outlined in WO 98/39474. The sample comprising fetal DNA is HLA typed for alleles not present in the mother using multiple sets of PCR primers designed to amplify specific HLA alleles followed by the detection of amplification products. Positive reactions (amplification products) will identify HLA alleles present in the fetal DNA but absent in the maternal DNA which can be used as fetal DNA/cell markers.

If commercial SSP kits are utilized (for instance using Olerup SSP™ HLA products, Qiagen AS, Norway) the reaction products will include maternal amplified alleles. However, since the HLA type of the mother has been determined the relevant amplification products can be discounted as non-fetal specific amplification products.

Example 3 (Prophetic)

Fetal DNA Quantitation Procedure Using HLA Type-Specific Standard Curve

Stocks of HLA-type specific DNA samples are prepared from genomic DNA of blood donors, and their exact DNA quantity is determined by standard (spectrophotometric or chemical) methods. The stocks are stored as single-use aliquots.

In the instance where fetal HLA typing from maternal plasma using a method of the invention has revealed HLA-A29 to be a unique fetal allele of the fetus a 1:3 dilution series from a stored aliquot of HLA-A29 standard DNA is made, covering a range from 5 ng to 1 pg DNA (=standard curve). A PCR primer pair is chosen that is specific for HLA-A29, for example; Forward CCCACTCCATGAGGTATTTCA (SEQ ID NO:13) and Reverse CTCCTGCTCTATCCACGGT (SEQ ID NO:14). Real-time quantitative PCR reactions are set up, using the standard curve preparation as well as 3-5 replicates of an aliquot (5-40 ul) of the DNA prepared from the maternal plasma (=test samples).

Reactions are carried out in a real-time Q-PCR apparatus (for example, Stratagene Mx3000P quantitative thermal cycler), using optimised conditions as determined for the HLA-A29 primer pair used. For example, the reaction may comprise (final concentration) 12.5 pmoles of each primer, 1×PCR buffer (Invitrogen) i.e: 20 mM Tris-HCl (pH 8.4), 50 mM KCl, 1 to 6 mM $MgCl_2$, 0.01 to 1.0 µM molecular beacon or for SYBR Green detection 0.05 to 2 times the supplied concentration (#S-9430, Sigma, USA), 200 µM dNTPs, Hot-Star Taq (0.625 units) (Qiagen GmbH, Germany). Cycling is performed with an initial denaturation step of 95° C. for 15 minutes followed by 50 cycles of 95° C. for 20 seconds, 62° C. for 30 seconds and 72° C. for 20 seconds. A final extension step is carried out at 72° C. for 2 minutes before cooling to ambient temperature. In the case of SYBR detection a denaturation curve is generated by the Mx3000P instrument in order to validate the product formed.

The accumulation of PCR product is measured by SYBR green or any hybridisation-based dye (beacon) system designed for the targeted amplicon. An example of a suitable molecular beacon for detecting amplification of the HLA-A29 allele is GCTCGGGTGACGACACGCAGTTCGT-GCGGACCGAGC (SEQ ID NO:17) which is labelled with a 5' fluorophore—HEX and a 3' quencher—BHQ1. The numbers of PCR cycles needed to reach a set amount of PCR product (signal threshold) is determined (=Ct). Ct is a function of the number of target sequences initially present in the samples. The processing by the real-time Q-PCR apparatus relates the Ct from the test samples to the Ct from the standard curve (with known DNA quantities), to yield the quantity of HLA-A29 DNA in the test samples. The concentration of fetal DNA (HLA-A29) in the maternal plasma sample is determined by calculating back through the dilution factors to the amount of sample used.

Example 4 (Prophetic)

Fetal DNA Quantitation Using a Universal Primer for the Standard Curve

This procedure is in essence as the one outlined above in Example 3, except that the standard curve is based on the PCR amplification of a non-polymorphic sequence (=universal standard), thus utilising the same DNA stock for all standard curves, instead of one DNA stock for each HLA type. To correct for differences in the PCR amplification efficiencies, a set of "relative efficiency factors" is determined experimentally, relating amplification efficiency for the universal standard to the efficiency of each of the HLA-type specific amplifications with the optimised primers and conditions.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which as been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Ahn, S. J. et al. (1996) Nucl. Acids Res. 13; 2623-25.
Al-Mufti, R. et al. (1999) Am. J. Med. Genet. 85; 66-75.
Bianchi, D. W. (2000) Eur. J. Obstet. Gynec. 92; 103-8.
Batova, I. N. et al. (1993) Biochem. Mol. Biol Int. 29; 451-66.
Douglas, G. W. et al. (1959) Am. J. Obstet. Gynec. 78; 960-73.
Gerlach, J. A. (2002) Arch. Pathol. Lab. Med. 126; 281-4.
Gibson, U. E. et al. (1996) Genome Res. 6; 995-1001
Hahn, S. et al. (2001) Ann. NY Acad. Sci. 945; 141-5.
Honda, H. et al. (2002) Hum. Genet. 110:75-9.
Hui, K. M. and Bidwell, J. L. (Eds) (1993) Handbook of HLA Typing Techniques, CRC Press.
Lee, T. et al. (2002) Am. J. Obstet Gynec. 187; 1217-21.
Leung, T. N. et al. (1998) Lancet 352; 1904-5.
Lo, Y. M. D. et al. (1997) Lancet 350; 485-7.
Lo, Y. M. D. et al. (1998) N. Engl. J. Med. 339; 1734-8.
Lo, Y. M. D. et al. (1999) Clin. Chem. 45; 184-8.
Lo, Y. M. D. (2000) Clin. Chem. 46; 1903-6.
Marsh, S. G. E. (2002) Tissue Antigens 60:407-64.
Middleton, D. (2000) Hum Immunol 61; 1285-97.
Middleton, D. et al. (2002) ASHI Quaterly 26; 112-3.
Mike, B. et al. (1997) Transplantation 64; 1505-13.
Parham, P. et al. (1999) The HLA FactsBook. Academic Press.
Pertl, B. and Bianchi, D. W. (2001) Obstet. Gynec. 98; 483-90.
Robinson, J. et al. (2003) Nucl. Acids Res. 31; 311-14.
Schroder, J. (1975) J. Med. Genet. 12; 230-42.
Wataganara, T. et al. (2003) Hum. Genet 112; 204-8.
Williams, F. (2002) Hum. Immunol. 63; 602-13.
Zhong, X. Y. et al. (2000) Prenat. Diag. 20; 838-41.
Zou, N. et al. (2003) Biotechniques 35; 758-60.

The invention claimed is:

1. A method of isolating fetal cells from a sample, the method comprising:
   (a) identifying an allele, encoding a polymorphic antigen, which allele is present in the DNA of the fetal cells but absent from maternal DNA, comprising
      i) obtaining a sample from the pregnant female comprising fetal and maternal nucleic acids, and
      ii) screening nucleic acids from the sample for at least one allele not present in the maternal cells,
   wherein the father is not typed for any alleles, wherein the allele is from a class I HLA locus, is HLA-A
   (b) binding to the fetal cell an affinity reagent which recognises the polymorphic antigen, and
   (c) selecting cells bound by the affinity reagent.

2. The method of claim 1, wherein the sample is obtained during the first trimester of pregnancy.

3. The method of claim 1, wherein if the pregnant female has not been typed for an allele before the method is performed the method further comprises typing alleles of at least one locus from maternal cells.

4. The method of claim 3, wherein the typing is performed by obtaining a genomic DNA sample from the pregnant female and exposing the DNA to amplification and/or sequencing procedures.

5. The method of claim 3, wherein the typing is performed by using antibodies which bind the protein products of specific alleles.

6. The method of claim 3, wherein typing alleles of at least one locus from maternal cells is performed on nucleated blood cells, saliva or hair follicles.

7. The method of claim 1, wherein the sample is derived from plasma, serum or urine.

8. The method of claim 1, wherein the sample is subjected to affinity chromatography to enrich nucleic acids from the sample.

9. The method of claim 1, wherein numerous potential alleles at a particular locus are investigated in the sample simultaneously by a multiplex amplification procedure.

10. The method of claim 1, wherein nucleic acid in the sample is DNA or RNA.

11. The method of claim 1, wherein the pregnant female is a mammal.

12. The method of claim 11, wherein the mammal is a human.

13. The method of claim 1, wherein the affinity reagent which recognises the antigen is an antibody.

14. The method of claim 13, wherein the antibody is detectably labelled.

15. A method of isolating fetal cells from a sample, the method comprising
   (a) identifying an allele, encoding a polymorphic antigen, which allele is present in the DNA of a fetal cell but absent from maternal DNA comprising;
      i) obtaining a sample from a pregnant female comprising fetal and maternal nucleic acids,
      ii) typing at least one locus from the sample obtained in step i),
      iii) comparing the alleles identified in step ii) with alleles of the same locus possessed by the pregnant female, and
      iv) selecting an allele typed in step iii) which is not possessed by the pregnant female, wherein the father is not typed for any alleles, and wherein the allele is from a class I HLA locus is HLA-A,
   (b) binding to the fetal cell an affinity reagent which recognises the polymorphic antigen, and
   (c) selecting cells bound by the affinity reagent.

* * * * *

UNITED STATES PATENT AND TRADEMARK OFFICE
CERTIFICATE OF CORRECTION

PATENT NO. : 8,394,582 B2
APPLICATION NO. : 10/547721
DATED : March 12, 2013
INVENTOR(S) : Ralph Michael Bohmer It is certified that error appears in the above-identified patent and that said Letters Patent is hereby corrected as shown below:

In the Claims:

In Claim 1, Col. 31, line 36, please delete "is HLA-A" and insert --and wherein the class I HLA locus is HLA-A,--

In Claim 15, Col. 32, line 54, please delete "is HLA-A," and insert --and wherein the class I HLA locus is HLA-A,--

Signed and Sealed this
Twenty-first Day of May, 2013

Teresa Stanek Rea
*Acting Director of the United States Patent and Trademark Office*